(12) United States Patent
Robie

(10) Patent No.: US 8,192,492 B2
(45) Date of Patent: Jun. 5, 2012

(54) SPINAL IMPLANT

(75) Inventor: Bruce Robie, Glen Rock, NJ (US)

(73) Assignee: Zimmer Spine, Inc., Minneapolis, MN (US)

( * ) Notice: Subject to any disclaimer, the term of this patent is extended or adjusted under 35 U.S.C. 154(b) by 1128 days.

(21) Appl. No.: 11/770,087

(22) Filed: Jun. 28, 2007

(65) Prior Publication Data

US 2008/0200985 A1    Aug. 21, 2008

Related U.S. Application Data

(62) Division of application No. 29/277,225, filed on Feb. 19, 2007, now Pat. No. Des. 566,842.

(51) Int. Cl.
*A61F 2/00* (2006.01)
(52) U.S. Cl. .................................................. 623/17.11
(58) Field of Classification Search ...... 623/17.11–17.16
See application file for complete search history.

(56) References Cited

U.S. PATENT DOCUMENTS

| | | | |
|---|---|---|---|
| D229,175 S | 11/1973 | Liberstone et al. | |
| D283,831 S | 5/1986 | Maddock | |
| 5,306,309 A | 4/1994 | Wagner et al. | |
| 5,522,899 A | 6/1996 | Michelson | |
| 5,534,028 A | 7/1996 | Bao et al. | |
| D377,527 S | 1/1997 | Michelson | |
| 5,776,199 A | 7/1998 | Michelson | |
| 5,810,825 A | 9/1998 | Huebner | |
| 5,888,222 A | 3/1999 | Coates et al. | |
| 5,989,289 A | 11/1999 | Coates et al. | |
| 6,096,080 A | 8/2000 | Nicholson et al. | |
| D433,750 S | 11/2000 | Burrows | |
| 6,143,033 A * | 11/2000 | Paul et al. | 623/17.11 |
| 6,371,988 B1 | 4/2002 | Pafford et al. | |
| 6,423,095 B1 | 7/2002 | Van Hoeck et al. | |
| 6,425,920 B1 | 7/2002 | Hamada | |
| 6,447,544 B1 | 9/2002 | Michelson | |
| 6,458,159 B1 * | 10/2002 | Thalgott | 623/17.11 |
| 6,468,311 B2 | 10/2002 | Boyd et al. | |
| 6,503,279 B1 * | 1/2003 | Webb et al. | 623/17.16 |
| 6,520,993 B2 | 2/2003 | James et al. | |
| D472,972 S * | 4/2003 | Anderson | D24/155 |
| 6,638,310 B2 | 10/2003 | Lin et al. | |
| 6,733,535 B2 | 5/2004 | Michelson | |
| 6,746,484 B1 | 6/2004 | Liu et al. | |
| 6,749,636 B2 | 6/2004 | Michelson | |
| 6,800,093 B2 | 10/2004 | Nicholson et al. | |
| D497,993 S | 11/2004 | Dixon et al. | |
| 6,964,687 B1 * | 11/2005 | Bernard et al. | 623/17.16 |

(Continued)

FOREIGN PATENT DOCUMENTS

WO    9909914 A1    3/1999

(Continued)

*Primary Examiner* — Eduardo C Robert
*Assistant Examiner* — Mary Hoffman
(74) *Attorney, Agent, or Firm* — Seager Tufte & Wickhem LLC

(57) ABSTRACT

A spinal implant as provided having a porous body that includes a leading end, a convex trailing end and first and second sides extending between the leading and trailing ends. At least a portion of the leading end is generally straight. The body further includes a generally dome-shaped superior surface and a generally planar inferior surface. The superior surface is convex between the leading and trailing ends and is convex between the first and second sides.

14 Claims, 3 Drawing Sheets

U.S. PATENT DOCUMENTS

| | | |
|---|---|---|
| 7,048,765 B1 | 5/2006 | Grooms et al. |
| 7,238,203 B2 * | 7/2007 | Bagga et al. ............... 623/17.11 |
| D553,742 S | 10/2007 | Park |
| 7,749,272 B2 | 7/2010 | Robie et al. |
| 2002/0106393 A1 | 8/2002 | Bianchi et al. |
| 2003/0023306 A1 | 1/2003 | Liu et al. |
| 2003/0125739 A1 | 7/2003 | Bagga et al. |
| 2004/0068320 A1 * | 4/2004 | Robie et al. ................. 623/17.16 |
| 2004/0133279 A1 | 7/2004 | Krueger et al. |
| 2004/0199251 A1 | 10/2004 | McCombe et al. |
| 2004/0230306 A1 | 11/2004 | Hoeck et al. |
| 2004/0230308 A1 | 11/2004 | Michelson |
| 2005/0004672 A1 | 1/2005 | Pafford et al. |
| 2005/0119753 A1 | 6/2005 | McGahan et al. |
| 2005/0149188 A1 | 7/2005 | Cook et al. |
| 2005/0171606 A1 | 8/2005 | Michelson |
| 2005/0222682 A1 | 10/2005 | Link et al. |
| 2005/0240267 A1 | 10/2005 | Randall et al. |
| 2005/0251257 A1 | 11/2005 | Mitchell et al. |
| 2006/0100705 A1 | 5/2006 | Puno et al. |
| 2006/0190082 A1 | 8/2006 | Keller et al. |
| 2006/0241763 A1 * | 10/2006 | Paul et al. .................. 623/17.11 |
| 2006/0247772 A1 | 11/2006 | McKay |

FOREIGN PATENT DOCUMENTS

| | | |
|---|---|---|
| WO | 0007528 A1 | 2/2000 |
| WO | 02091909 A2 | 11/2002 |

\* cited by examiner

US 8,192,492 B2

SPINAL IMPLANT

CROSS REFERENCE

This application claims priority to U.S. Design patent application Ser. No. 29/277,225, "Spinal Implant", filed Feb. 19, 2007, the disclosure of which is expressly incorporated by reference herein in its entirety.

FIELD OF THE INVENTION

The present invention relates generally to skeletal implants. More particularly, the present invention relates to implants for stabilizing intervertebral joints.

BACKGROUND OF THE INVENTION

Chronic back problems cause pain and disability for a large segment of the population. In many cases, chronic back problems are caused by intervertebral disc disease. When an intervertebral disc is diseased, the vertebrae between which the disc is positioned may be inadequately supported, resulting in persistent pain. Stabilization and/or arthrodesis of the intervertebral joint can reduce the pain and debilitating effects associated with disc disease.

Spinal stabilization systems and procedures have been developed to stabilize diseased intervertebral joints and, in some cases, to fuse the vertebrae that are adjacent the diseased joint space. Most fusion techniques include removing some or all of the disc material from the affected joint, and stabilizing the joint by inserting an implant (e.g., a bone graft or other material to facilitate fusion of the vertebrae) in the cleaned intervertebral space.

Spinal implants can be inserted into the intervertebral space through an anterior approach, a lateral (transverse) approach, a posterior approach, or postero-lateral approach. The anterior approach involves a surgeon seeking access to the spine through the front (i.e., abdominal area) of the patient. The posterior approach involves a surgeon seeking access to the spine through the back of the patient. The postero-lateral approach is similar to the posterior approach with access coming more from either or both sides of the patient. A variety of different anterior, posterior and posterior-lateral techniques are known.

SUMMARY OF THE INVENTION

While the invention will be described in connection with certain embodiments, it will be understood that the invention is not limited to these embodiments. On the contrary, the invention includes all alternatives, modifications and equivalents as may be included within the spirit and scope of the present invention.

A spinal implant is provided having a porous body that includes a leading end, a convex trailing end and first and second sides extending between the leading and trailing ends. At least a portion of the leading end is generally straight. The body also includes a generally dome-shaped superior surface and a generally planar inferior surface. The superior surface is convex between the leading and trailing ends and is convex between the first and second sides.

In other embodiments, the implant may include one or more of the following features. The implant may further include a first opening extending through the implant from the superior surface to the inferior surface and a second opening communicating with the first opening and extending through the trailing end. The first and second openings are configured for receipt of an inserter instrument to insert the implant between vertebral bodies.

The inferior surface may have a generally trapezoidal shape. The first and second sides may be generally straight and may diverge away from one another from the leading end to the trailing end. The body may be made of metal. The leading end may be a posterior end and the trailing end may be an anterior end.

BRIEF DESCRIPTION OF THE DRAWINGS

The accompanying drawings, which are incorporated in and constitute a part of this specification, illustrate embodiments of the invention and, together with a general description of the invention given above, and a detailed description of the embodiments given below, serve to explain the principles of the invention.

DETAILED DESCRIPTION

Figure 1:
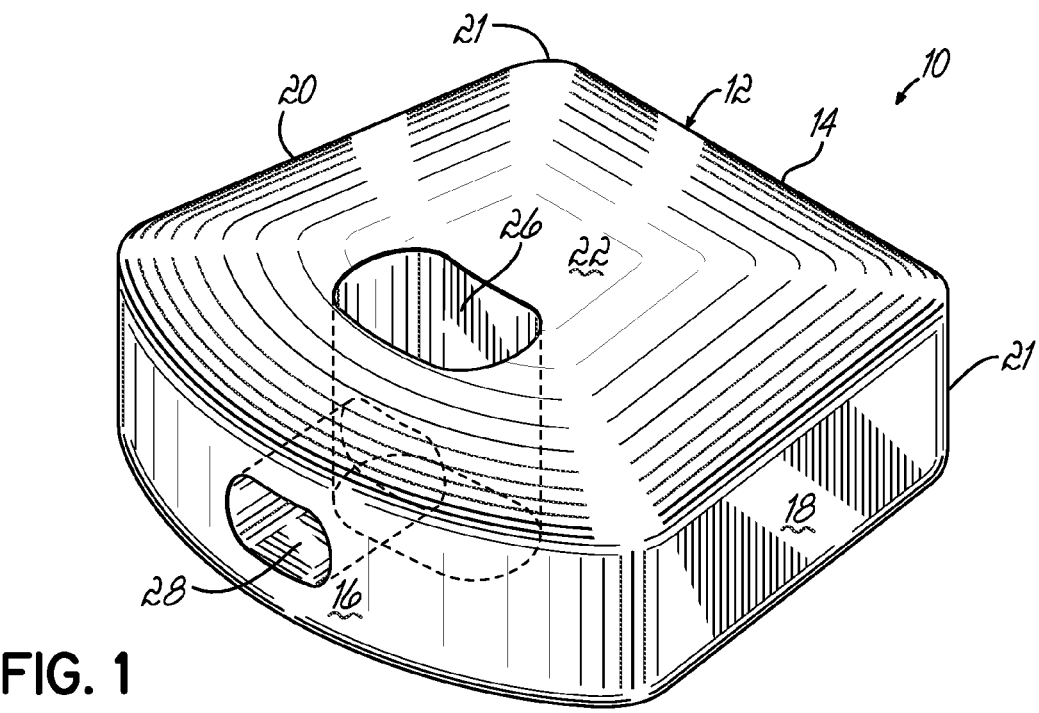
FIG. 1 is a front perspective view of a spinal implant according to one embodiment of the present invention.

The present invention is directed to skeletal implants and methods for placing implants between bones desired to be fused. It is preferred for the implants to be used for vertebral/spinal applications such as fusing cervical, thoracic and/or lumbar intervertebral joints. In the case of fusing an intervertebral joint, implants in accordance with the principles of the present invention can be implanted using an anterior, posterior or postero-lateral approach to the patient's vertebrae.

As used herein, an "implant" includes any implant suitable for facilitating fusion between adjacent bones and includes implants prepared from known implant materials including, non-bone material such as titanium, stainless steel, porous tantalum or other metal, bio-glass, calcium phosphate, ceramic, carbon fiber-based polymers and biodegradable polymers.

FIGS. 1-7 illustrate a spinal implant 10 according to one embodiment of the present invention. Implant 10 includes a body 12 having a leading end 14, a convex trailing end 16 and first 18 and second 20 sides that extend between the leading 14 and trailing 16 ends. Leading end 14 may include rounded, or radiused portions, indicated at 21, that blend with sides 18, 20. Leading end 14 may be generally straight between the rounded portions 21. The body 12 further includes a generally dome-shaped superior surface 22 and an inferior surface 24 that may be generally flat. The superior surface is convex between the leading 14 and trailing 16 ends and is also convex between sides 18, 20. Accordingly, the superior surface is convex in both an anterior-to-posterior direction and a medial-to-lateral direction.

Implant 10 further includes an opening 26 that extends completely through implant 10 from the superior surface 22 to the inferior surface 24. Implant 10 also includes an opening 28 that communicates with opening 26 and extends through the trailing end 16. The function of openings 26, 28 are described below. In an exemplary embodiment, openings 26 and 28 may be generally oval-shaped. However, one or both of openings 26, 28 may have other shapes within the scope of the present invention.

Figure 2:
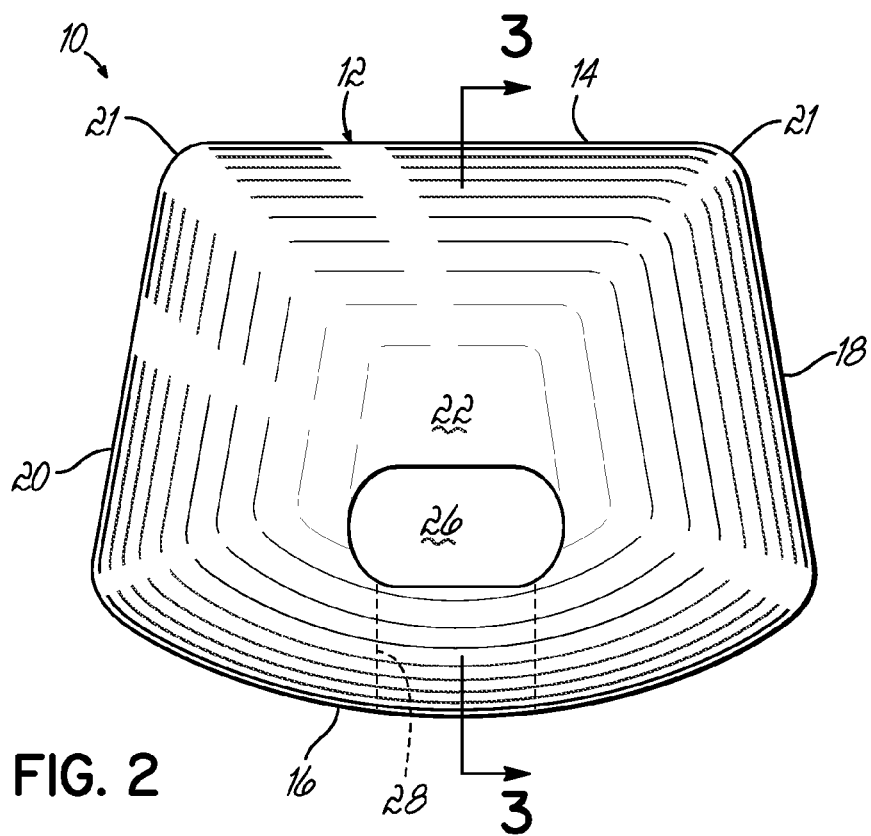
FIG. 2 is a top plan view of the implant shown in FIG. 1.
Figure 3:
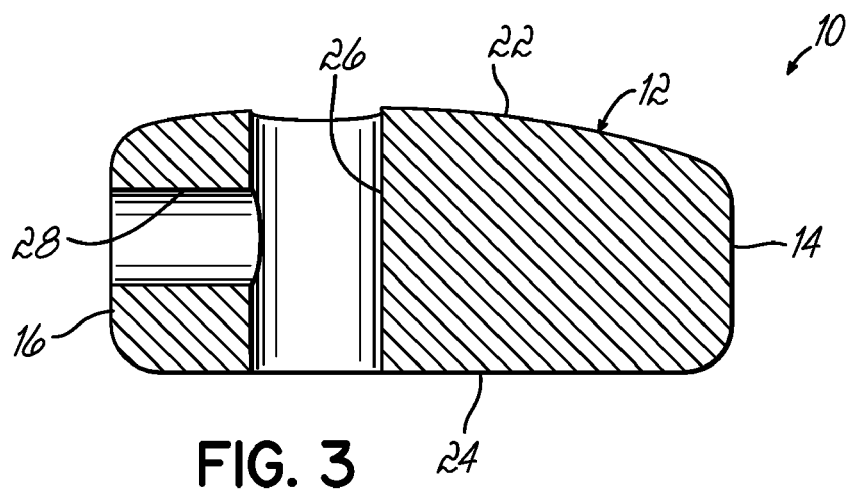
FIG. 3 is a cross-sectional view taken along line 3-3 in FIG. 2.
Figure 4:
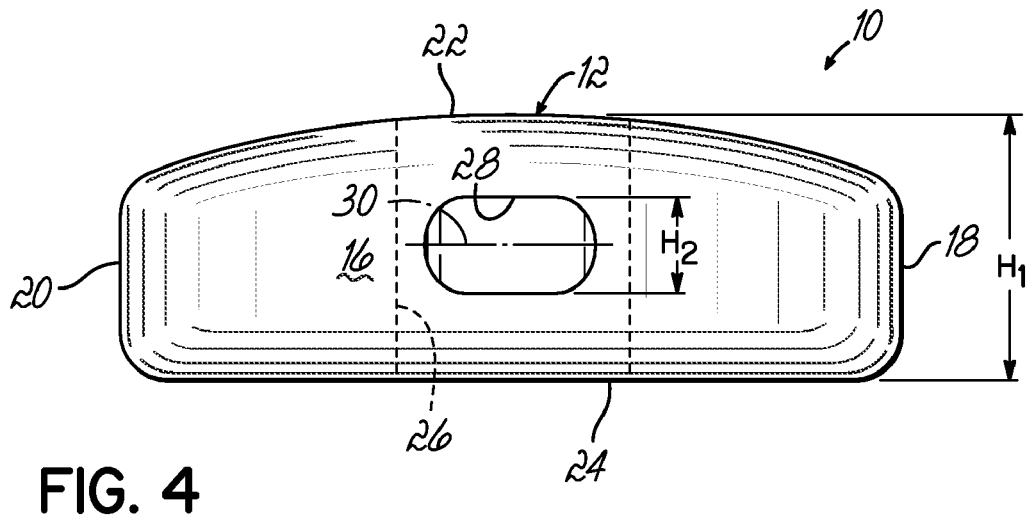
FIG. 4 is a front elevational view of the implant shown in FIGS. 1-3.
Figure 5:
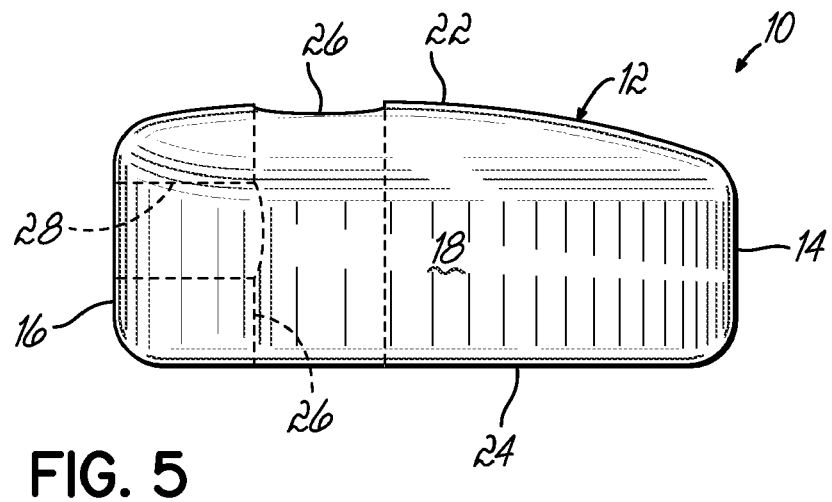
FIG. 5 is a side elevational view of the implant shown in FIGS. 1-4.
Figure 6:
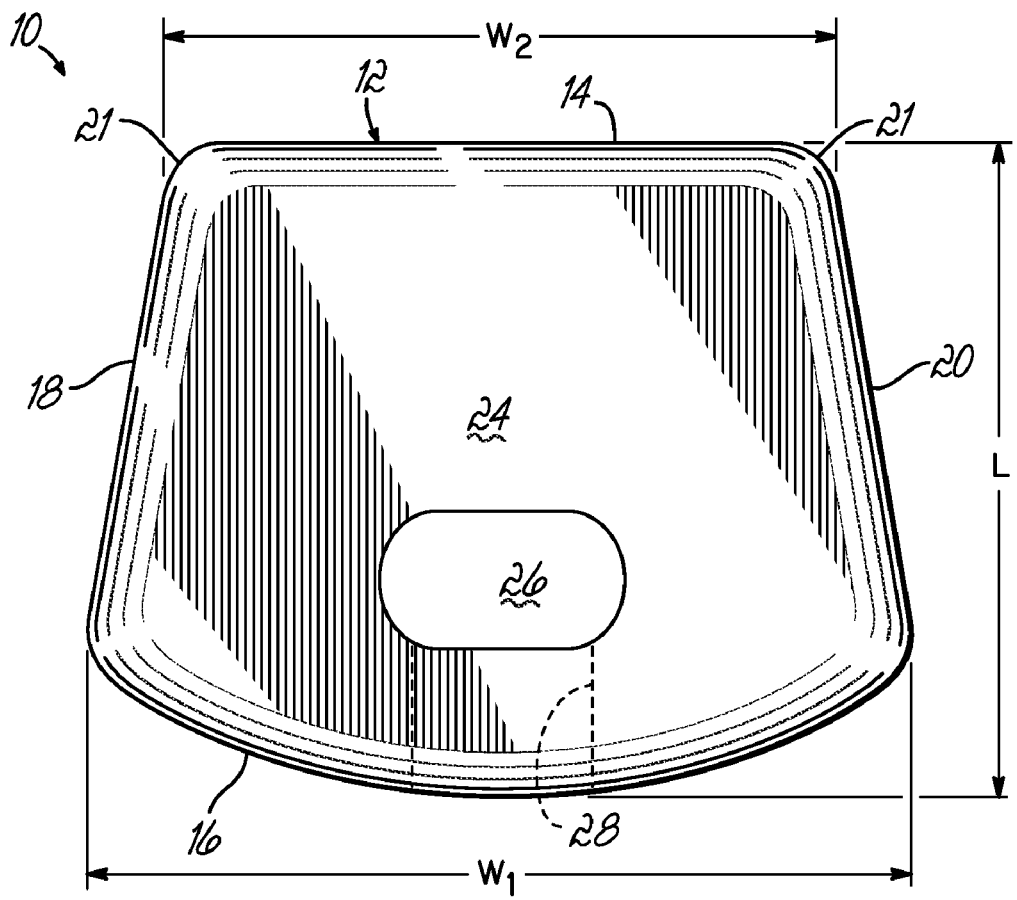
FIG. 6 is a bottom view of the implant shown in FIGS. 1-5.
Figure 7:
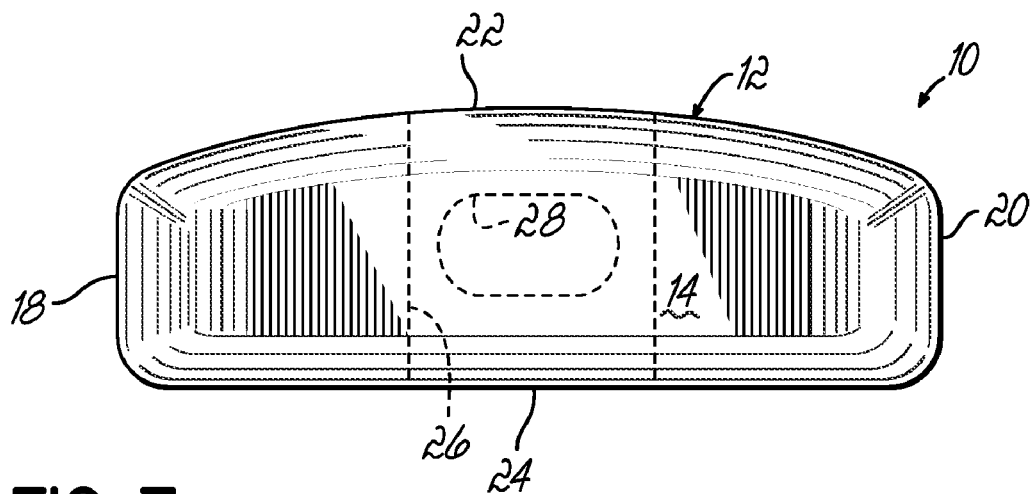
FIG. 7 is a rear elevational view of the implant shown in FIGS. 1-6.

As shown in FIG. 4, implant 10 has a height "$H_1$" extending between the highest point on the superior surface 22 and the inferior surface 24. Implant 10 also includes length "L" that extends between the leading end 14 and the location on trailing end 16 that is the farthest away from leading end 14. A first width "$W_1$" exists between sides 18, 20 at the trailing end 16 and a second width "$W_2$" exists between sides 18, 20 at the leading end 14. Sides 18 and 20 may diverge away from one another between the leading 14 and trailing 16 ends, as shown in FIGS. 2 and 6. Accordingly, the inferior surface 24 has a generally trapezoidal shape and width "$W_1$" is greater than width "$W_2$". The magnitudes height "H", length "L" and widths "$W_1$" and "$W_2$" may vary with application.

In an exemplary embodiment, implant 10 may be inserted into a cervical disc space to fuse adjacent cervical vertebrae. Also, in an exemplary embodiment, implant 10 may be inserted using an anterior approach, such that leading end 14 is a posterior end and trailing end 16 is an anterior end. In this event, a distal end, or key of an instrument, such as an inserter (not shown) may be inserted into opening 28 such that a width of the key initially extends generally along a longitudinal axis 30 of opening 28. When the inserter is inserted farther into implant 10, the key of the inserter reaches the intersection of openings 26 and 28. The inserter may then be rotated 90 degrees such that the width of the key extends along the length of opening 26 partially between the superior 22 and inferior 24 surfaces. The width of the inserter key is sized such that it is greater than a height "$H_2$" of opening 28, which releasably secures the inserter to implant 10. The inserter may be removed by rotating it 90 degrees which generally aligns the width of the key with the longitudinal axis 30 of opening 28, and then retracting the inserter from implant 10.

In an exemplary embodiment, when implant 10 is used to fuse adjacent cervical vertebrae, the generally trapezoidal shape of inferior surface 24, including the rounded portions 21 of leading end 14, may match the general shape of cervical vertebral bodies. Also, in this exemplary embodiment, the dome-shaped superior surface 22 may generally match cervical endplate anatomy and the generally flat inferior surface 24 may mate with a flat inferior endplate in the cervical disc space or a surgically-created flat surface of a vertebral body during a hemi-vertebrectomy. Body 10 may be made from a metal, which may be a porous metal. The use of a porous metal enhances bony ingrowth. One example of such a material is Trabecular Metal™, which is marketed by Zimmer Spine, Inc., of Edina, Minn. Embodiments of this material are also described in several U.S. patents, including, for example, U.S. Pat. Nos. 5,443,515 and 6,063,042, each disclosure of which is expressly incorporated by reference herein in its entirety.

Implants 10 may be inserted by a variety of surgical approaches, including, but not limited to an anterior approach, a lateral (transverse) approach, a posterior approach, or postero-lateral approach by engaging the implant 10 with an instrument, such as an inserter. In the exemplary embodiment of implant 10 illustrated in FIGS. 1-7 and discussed above, openings 26 and 28 may be used to receive an inserter. However, in other embodiments, implant 10 may include grooves, indentations, slots or other surface deficits that allow the inserter to engage implant 10. For example, the trailing end 16 of body 12 of implant 10 may include holes, such as a circular hole or holes that mate with prongs on the inserter. Alternatively, body 12 may include two or more square or rectangular surface deficits cut into the superior 22 and inferior 24 surfaces proximate trailing end 16 that may be engaged by the inserter. In other embodiments, slots or grooves may be formed in each of the sides 18, 20. The slots or grooves may be partially formed into and engaged at the trailing end 16 by the inserter. The slots or grooves may be formed such that a portion of the implant 10 forms a positive stop for the inserter instrument. Alternatively, the slots or grooves may extend the length of the sides 18, 20 of body 12.

While the present invention has been illustrated by the description of and exemplary embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicants' general inventive concept.

What is claimed is:

1. A spinal implant comprising:
a porous body comprising a leading end, a convex trailing end and first and second sides extending between said leading and trailing ends, at least a portion of said leading end being generally straight, the body having a leading portion and a trailing portion defined by a midline dividing a length of the body in half;
said body further comprising:
a generally dome-shaped superior surface, said superior surface being convex between said leading and trailing ends and convex between said first and second sides;
a generally planar inferior surface; and
an opening having a first portion extending through said trailing end to a location within the trailing portion, and a second portion extending toward said superior surface and toward said inferior surface, the entire opening located within the trailing portion.

2. The implant of claim 1,
wherein the first portion of the opening has a height and a width, wherein the height is smaller than the width, wherein the first and second portions of the opening are configured for receipt of an inserter instrument to insert the implant between vertebral bodies.

3. The implant of claim 1, wherein:
said inferior surface has a generally trapezoidal shape.

4. The implant of claim 1, wherein:
said first and second sides are generally straight and diverge away from one another from the leading end to the trailing end.

5. The implant of claim 1, wherein:
said body is made of metal.

6. The implant of claim 1, wherein:
said leading end is a posterior end and said trailing end is an anterior end.

7. A spinal implant comprising:
a porous body comprising a leading end, a convex trailing end and first and second sides extending between said leading and trailing ends, at least a portion of said leading end being generally straight, the body having a length extending between the leading end and the furthest point on the trailing end, the body having a leading portion and a trailing portion defined by a midline dividing the length in half;
said body further comprising:

a generally dome-shaped superior surface, said superior surface being convex between said leading and trailing ends and convex between said first and second sides;
a generally planar inferior surface;
a first opening extending through said implant from said superior surface to said inferior surface, the entire first opening located within the trailing portion; and
a second opening communicating with said first opening and extending through said trailing end, the first and second openings configured for receipt of an inserter instrument to insert the implant between vertebral bodies.

8. The implant of claim 7, wherein:
said inferior surface has a generally trapezoidal shape.

9. The implant of claim 7, wherein:
said first and second sides are generally straight and diverge away from one another from the leading end to the trailing end.

10. The implant of claim 7, wherein:
said body is made of metal.

11. A spinal implant comprising:
a porous body comprising a leading end, a convex trailing end and first and second sides extending between said leading and trailing ends, at least a portion of said leading end being generally straight;
said body further comprising:
a generally dome-shaped superior surface, said superior surface being convex between said leading and trailing ends and convex between said first and second sides;
a generally planar inferior surface;
a first opening extending through said implant from said superior surface to said inferior surface, wherein the superior and inferior surfaces each define a surface area of the body, said first opening occupying substantially less than half the surface area of the body; and
a second opening communicating with said first opening and extending through said trailing end, the first and second openings configured for receipt of an inserter instrument to insert the implant between vertebral wherein the body has a length extending between the leading end and the furthest point on the trailing end, the body having a leading portion and a trailing portion defined by a midline dividing the length in half, the entire first opening located within the trailing portion.

12. The implant of claim 11, wherein:
said inferior surface has a generally trapezoidal shape.

13. The implant of claim 11, wherein:
said first and second sides are generally straight and diverge away from one another from the leading end to the trailing end.

14. The implant of claim 11, wherein:
said body is made of metal.

\* \* \* \* \*